(12) United States Patent
Gadgil et al.

(10) Patent No.: US 11,988,601 B2
(45) Date of Patent: May 21, 2024

(54) METHOD FOR DETERMINING RESIDUAL CARBAMATE COMPOUNDS ON AN ELASTOMERIC ARTICLE

(71) Applicants: Kimberly-Clark Worldwide, Inc., Neenah, WI (US); Alison S. Bagwell, Alpharetta, GA (US)

(72) Inventors: Priyadarshini Gadgil, Roswell, GA (US); Alison S. Bagwell, Alpharetta, GA (US); Maurice Thompson, Duluth, GA (US); Zamsari Bin Zakaria, Subang Jaya (MY); Sumsuriya Beraheng, Subang Jaya (MY)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 17/289,534

(22) PCT Filed: Jun. 8, 2020

(86) PCT No.: PCT/US2020/036560
§ 371 (c)(1),
(2) Date: Apr. 28, 2021

(87) PCT Pub. No.: WO2021/251941
PCT Pub. Date: Dec. 16, 2021

(65) Prior Publication Data
US 2022/0205907 A1    Jun. 30, 2022

(51) Int. Cl.
| | |
|---|---|
| *G01N 21/25* | (2006.01) |
| *G01N 21/27* | (2006.01) |
| *G01N 21/29* | (2006.01) |
| *G01N 21/35* | (2014.01) |
| *G01N 21/3563* | (2014.01) |
| *G01N 33/44* | (2006.01) |

(52) U.S. Cl.
CPC ......... *G01N 21/3563* (2013.01); *G01N 21/29* (2013.01); *G01N 33/442* (2013.01); *G01N 2021/3572* (2013.01)

(58) Field of Classification Search
CPC .... G01N 21/25; G01N 21/3563; G01N 33/44; G01N 33/442; G01N 21/29; G01N 21/27
USPC ......................................................... 436/85
See application file for complete search history.

(56) References Cited

U.S. PATENT DOCUMENTS

| | | | | |
|---|---|---|---|---|
| 3,351,570 A * | 11/1967 | Bruce | ......................... | C08J 9/36 521/70 |
| 3,647,683 A * | 3/1972 | Kelly | ..................... | C10G 27/12 208/195 |
| 3,785,813 A * | 1/1974 | Rickter | .................... | G03C 8/16 430/505 |
| 3,898,042 A * | 8/1975 | Webb | ................. | G01N 33/1813 422/62 |
| 3,964,994 A * | 6/1976 | Kelly | ..................... | C10G 27/12 208/180 |
| 4,062,906 A * | 12/1977 | Knight | .................... | C08C 19/22 524/576 |
| 6,051,320 A * | 4/2000 | Noecker | .................... | C08J 5/02 428/447 |
| 6,383,552 B1 * | 5/2002 | Noecker | ................... | C08L 7/02 428/447 |
| 6,624,274 B1 * | 9/2003 | Suddaby | ................. | C08L 13/02 526/318 |
| 9,018,341 B2 | 4/2015 | Paping et al. | | |
| 10,125,239 B2 | 11/2018 | Chen et al. | | |
| 10,137,475 B2 | 11/2018 | Li et al. | | |
| 2003/0088002 A1 * | 5/2003 | Dzikowicz | ............... | C08K 5/47 524/508 |
| 2003/0201224 A1 * | 10/2003 | Gannon | .................. | C02F 3/345 435/252.4 |
| 2004/0063832 A1 * | 4/2004 | Dzikowicz | ............... | C08K 5/47 524/508 |
| 2007/0031972 A1 | 2/2007 | Attar | | |
| 2007/0100081 A1 * | 5/2007 | Suddaby | ................... | C08J 5/02 525/331.9 |
| 2007/0105971 A1 * | 5/2007 | Schaller | ..................... | C08J 3/26 427/430.1 |
| 2009/0192244 A1 * | 7/2009 | Doyle | ........................ | C08C 1/04 524/575.5 |
| 2009/0292081 A1 * | 11/2009 | Suddaby | .............. | C08K 5/0091 525/370 |

(Continued)

FOREIGN PATENT DOCUMENTS

| | | | | |
|---|---|---|---|---|
| CN | 102914604 A | | 2/2013 | |
| CN | 106124279 A | * | 11/2016 | ............... G01N 1/28 |

(Continued)

OTHER PUBLICATIONS

Shepard, A. F. et al., Industrial and Engineering Chemistry 1934, 26, 1200-1201. (Year: 1934).*
Jarrijon, A., Rubber Chemistry and Technology 1946, 19, 1061-1076. (Year: 1946).*
Schaefer, w., Rubber Chemistry and Technology 1950, 23, 292-299. (Year: 1950).*
Kulberg, L. M. et al., Rubber Chemistry and Technology 1952, 25, 152-156. (Year: 1952).*
Fischer, W., Fresenius' Zeitschrift für Analytische Chemie 1952, 137, 90-98. (Year: 1952).*

(Continued)

*Primary Examiner* — Arlen Soderquist
(74) *Attorney, Agent, or Firm* — Dority & Manning, P.A.

(57) ABSTRACT

A method and process for determining the propensity of elastomeric articles to discolor or stain is provided. The elastomeric articles tested are generally crosslinked elastomeric articles containing accelerators, such as carbamates. Residual carbamates can cause staining when contacted with metal ions, such as copper. Tests are disclosed for determining the propensity of the elastomeric articles to stain or discolor. The process can include remediation steps for preventing future articles from staining.

6 Claims, 2 Drawing Sheets

(56) References Cited

U.S. PATENT DOCUMENTS

| | | | | |
|---|---|---|---|---|
| 2011/0229668 A1* | 9/2011 | Doyle | .................... | C08J 5/02 521/65 |
| 2019/0085157 A1* | 3/2019 | Kim | .................... | A41D 19/00 |
| 2019/0177496 A1 | 6/2019 | Chen et al. | | |

FOREIGN PATENT DOCUMENTS

| | | | | |
|---|---|---|---|---|
| CN | 106350447 B | | 1/2017 | |
| CN | 106770878 B | | 6/2018 | |
| CN | 108693126 A | | 10/2018 | |
| EP | 0614079 A2 | | 2/1993 | |
| EP | 1563000 A1 | | 5/2004 | |
| EP | 1925339 A1 | | 5/2008 | |
| EP | 1828400 B1 | | 7/2012 | |
| EP | 3039432 B1 | | 3/2015 | |
| GB | 1074041 A | * | 6/1967 | ............... C08J 7/00 |
| JP | H09318615 A | | 12/1997 | |
| SU | 1490608 A | * | 6/1989 | |
| WO | WO-2004044037 A1 | * | 5/2004 | ............ C08C 19/36 |
| WO | WO2011/059403 A1 | | 5/2011 | |
| WO | WO2016/076099 A1 | | 5/2016 | |

OTHER PUBLICATIONS

Parker, C. A. et al., Rubber Chemistry and Technology 1954, 27, 1013-1018. (Year: 1954).*
Scheele, W. et al., Rubber Chemistry and Technology 1958, 31, 301-314. (Year: 1958).*
Yuasa, T. et al., Japan Analyst 1964, 13, 966-970. (Year: 1964).*
Auler, H., Rubber Chemistry and Technology 1964, 37, 950-972. (Year: 1964).*
Yuen, C. S., Journal of Natural Rubber Research 1995, 10, 255-265. (Year: 1995).*
Tinkler, J. et al., Food and Chemical Toxicology 1998, 36, 849-846. (Year: 1998).*
Smeaton, J., Doctoral Thesis 1998, 272 pages. (Year: 1998).*
Knudsen, B. B. et al., Contact Dermatitis 2000, 43, 9-15. (Year: 2000).*
Depree, G. J. et al., Journal of Chromatographic Science 2004, 42, 80-84. (Year: 2004).*
Depree, G. J. et al., Contact Dermatitis 2005, 53, 107-113. (Year: 2005).*
Bergendorff, O. et al., Contact Dermatitis 2006, 55, 210-215. (Year: 2006).*
Gardner, N., Health & Safety International 2008, 77-82. (Year: 2008).*
Knudsen, B. B. et al., Contact Dermatitis 1993, 28, 63-69 (Year: 1993).*
Truscott, W., Medical Device & Diagnostic Industry Magazine 1996 4 pages, downloaded from https://www.mddionline.com/print/2430. (Year: 1996).*
Mathieu, C. et al., Journal of High Resolution Chromatography 2000, 23, 565-566. (Year: 2000).*
Abraham, E. K., Thesis 2005, 218 pages. (Year: 2005).*
Solvent Properties Table, downloaded May 18, 23 from https://www.chem.ucla.edu/~bacher/General/30BL/tips/solvent.html.*
Copper(II) acetate monohydrate product properties, Millipore Sigma, 2 pages, downloaded May 18, 23 from https://www.sigmaaldrich.com/US/en/product/aldrich/229601.*
Copper(II) acetate properties CemEurope.com, 2 pages, downloaded May 18, 23 from https://www.chemeurope.com/en/encyclopedia/Copper%28II%29_acetate.html.*
Fox, C. P. Journal of Industrial and Engineering Chemistry 1917, 9, 1092-1093. (Year: 1917).*
Zijp, J. W. H., Recueil des Travaux Chimiques des Pays-Bas 1956, 75, 1083-1088. (Year: 1956).*
Datta, R. N. et al., Rubber Chemistry and Technology 1986, 59, 27-39. (Year: 1986).*
Lee, C. et al., Analytical Biochemistry 1987, 166, 308-312. (Year: 1987).*
Hansson, C. et al., Con/act Dermatitis 1997, 36, 195-200. (Year: 1997).*
International Search Report Corresponding to Application No. PCT/US2020/036560 dated Mar. 5, 2021.
Jacob et al. "Residual Accelerator and Cyto-Toxicity Studies of NR Surgical Gloves", Rubber Science, India, 2016, pp. 322-343.
European Search Report Corresponding to Application No. 20939696.9 on Feb. 8, 2024.

* cited by examiner

METHOD FOR DETERMINING RESIDUAL CARBAMATE COMPOUNDS ON AN ELASTOMERIC ARTICLE

BACKGROUND

The development of modern rubber materials has made possible the manufacture of a wide range of elastomeric articles having varying properties of strength and chemical resistance. As synthetic latex materials have developed, various elastic and polymeric materials have been adapted for use in making a variety of articles of manufacture. One useful class of synthetic rubber material compounds includes the nitrile rubber class, which is widely used to make all different types of elastic articles. Such elastic articles can include, for instance, elastic seals, gloves, balloons, and condoms.

Due to various drawbacks to using natural rubber latex, many elastic articles are made from synthetic polymers such as nitrile rubber. In forming the elastic articles, the synthetic polymer can be formed into an emulsion that can be coated onto a mold for producing various different types of products. For example, nitrile rubber can be formed from a random terpolymer of acrylonitrile, butadiene, and a carboxylic acid such as methacrylic acid. The synthetic polymer is typically crosslinked during formation of the article. Crosslinking the polymer, for instance, can increase its strength and chemical resistance. Nitrile polymers, for instance, can be crosslinked by ionically bonding carboxylic acid groups together using multivalent metal ions, such as zinc oxide. Another type of crosslinking mechanism is a covalent crosslinking of the butadiene segments of the polymer using sulfur and catalysts known as rubber accelerators. In forming elastic articles, a coagulant solution is first applied to a mold followed by contacting the coagulant solution with a polymer latex.

Recently, due to various government regulatory changes, the use of accelerants in forming elastic articles has been reduced, modified, or altogether removed from the process. These changes, however, have caused the elastic articles to become susceptible to staining. Although staining of the article does not in any way impact its physical properties, the observation of stains can negatively impact the product by the consumer. Thus, a need currently exists for a method and process of determining the causation of staining and the susceptibility of the elastic article to staining so that remedial actions can be taken in order to prevent the articles from staining during use.

SUMMARY

The present disclosure is generally directed to a process for rapidly determining whether crosslinked elastomeric articles are susceptible to staining when placed in use. Due to regulatory changes, the amount of accelerants used in producing elastomeric articles has changes. These changes have led to an increased propensity of the articles to stain when in use, especially when the elastomeric articles are contacted with human skin or hands. Through extensive testing, it was discovered that staining is being caused by a reaction between residual carbamate accelerators on the elastomeric article and a metal, such as copper. The present disclosure is directed to a rapid method that can be used to determine residual accelerator amounts on elastomeric articles so that, if necessary, remedial actions can be taken during production of the articles to decrease the propensity of the articles to stain. Of particular advantage, the method can occur at the manufacturing site of the elastomeric article.

In one embodiment, for instance, the present disclosure is directed to a method for determining residual carbamate compounds in elastomeric articles. The method includes contacting an elastomeric article or an extract obtained from the elastomeric article with a metal solution, such as a transition metal solution. The metal solution can be, for instance, a copper solution, a cobalt solution and/or a nickel solution. In one aspect, the metal solution is a metal acetate solution, such as a copper acetate solution. The elastomeric article is then tested for staining.

In one aspect, the test for staining is a visual test for discoloration of the elastomeric article after being contacted with the metal acetate solution. For example, an observer can look for yellow discolorations. In this embodiment, the metal acetate solution is applied directly to a surface of the elastomeric article. The metal acetate solution, for instance, can be sprayed on the article or the article can be dipped into the solution.

In an alternative embodiment, the elastomeric article can be contacted with an extractant for producing an extract that is then contacted with the metal acetate solution. The extractant, for instance, can be an acetone solution. The elastomeric article can be contacted with the acetone solution for obtaining an extract. The metal acetate, such as copper acetate, can then be combined with the extract obtained from the elastomeric article. The resulting solution can then be tested for staining by measuring an absorbance of the extract and copper acetate solution at a predetermined wavelength using spectrophotometry. The wavelength, for instance, can be from about 200 nm to about 700 nm. In one embodiment, for instance, the extract and copper acetate solution is measured at a wavelength of 433 nm.

If desired, the absorbance measurement of the extract and copper acetate solution can then be compared to reference data in order to determine a concentration of residual carbamate that is present on the elastomeric article. The reference data may include a reference graph that plots absorbance at the wavelength measured versus carbamate concentration. In one aspect, the reference data can have a concentration range of from about 0 ppm to about 100 ppm.

The method of the present disclosure can be used to test for the presence of any residual carbamate compounds. In one aspect, the method can be tailored to measure concentrations of particular carbamate compounds, such as zinc diethyldithiocarbamate, zinc dibutyldithiocarbamate, or mixtures thereof.

In one aspect, the present disclosure is further directed to taking remedial action should residual carbamate levels be above a desired limit. The remedial action can include further washing steps of the elastomeric articles after being formed or can include adjusting accelerator levels during production of the article and/or increasing the use of crosslinking agents in order to decrease residual carbamate levels.

The method of the present disclosure is well suited for use with any suitable elastomeric article that is produced using an accelerator, such as a carbamate accelerator. For example, the method of the present disclosure can be applied to any butadiene-type elastomeric article, including elastomeric articles made from nitrile polymers. The articles that are tested in accordance with the present disclosure can include gloves, particularly cleanroom gloves, gaskets, seals, elastic bands, and the like.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
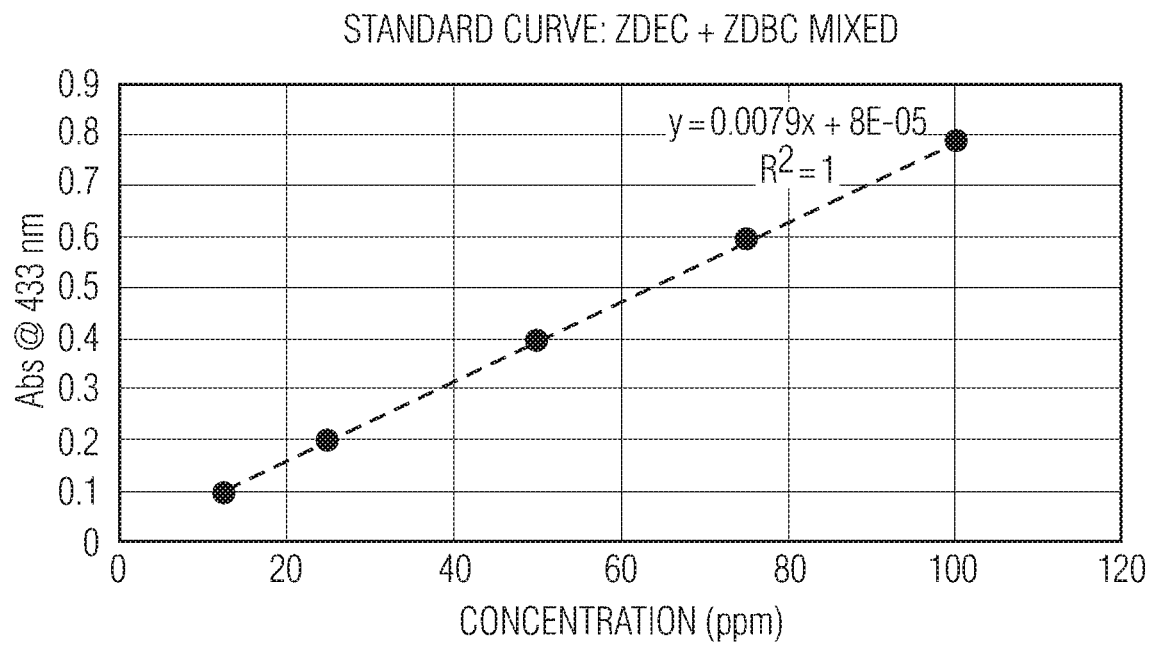
FIG. 1 is a graph illustrating absorbance versus concentration relationship for a mixture of zinc diethyldithiocarbamate and zinc dibutyldithiocarbamate.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

Recently, various changes have been made to rubber formulations used to make elastomeric articles. More particularly, due to various regulatory changes, elastomeric articles made from crosslinked rubber materials have recipes with modified amounts of accelerators and/or removal of certain accelerators. Although these changes generally have no impact on the physical properties of the elastomeric articles, the elastomeric articles are susceptible to staining which is disliked by consumers. Through extensive testing, it was discovered that the discoloration or staining is a result of residual carbamate accelerators present on the elastomeric articles. More particularly, it was discovered that elastomeric articles can discolor due to human contact, such as through contact with human perspiration. This discoloration translates into a feint yellow discoloration which develops through contact of metal ions, such as copper ions, and residual accelerators, particularly carbamates, that are contained in the elastomeric article. For instance, the discoloration can occur when human perspiration contacts the elastomeric article due to the metal ions that are present in perspiration. The amount of discoloration can be highly subjective as the content of chemical salts/ions in human perspiration can vary widely, causing either low to no effect on the visual appearance of the elastomeric article. Further, if the user is wearing jewelry, particularly copper-based jewelry, the elastomeric article is susceptible to a greater level of discoloration in that metal ions from jewelry can readily absorb into the surface of skin and is very challenging to remove even through good hand hygiene practices.

In view of the above, the present disclosure is directed to a quick and rapid method for determining accelerator or carbamate levels in elastomeric articles in order to determine whether the articles are susceptible to discoloration and staining. For example, the method of the present disclosure can be used to determine and control the amount of residual carbamates that are present in elastomeric articles. Of particular advantage, the method of the present disclosure does not require complicated scientific laboratory equipment such as an HPLC device. The method of the present disclosure can be performed in the manufacturing facility where the elastomeric articles are produced. The method can also be performed very quickly allowing for remedial actions to be taken in order to control residual carbamate levels if they rise above a desired level. In this manner, in one embodiment, the present disclosure is directed to a holistic process that can test for residual accelerator amounts on elastomeric articles quickly and immediately make process/formulation changes and adjustments based on the test results.

In general, any suitable elastomeric article formed with accelerators and/or carbamates can be tested in accordance with the present disclosure. For example, the elastomeric article can be made from a butadiene-type rubber. The method and process of the present disclosure is particularly well suited to testing elastomeric articles that have a lighter shade of color, such as white products, off-white products, gray products, blue products, clear products, semi-transparent or translucent products, and the like. The method and process of the present disclosure is also well suited to elastomeric articles having a relatively thin wall thickness, such as less than about 10 mm, such as less than about 5 mm, such as less than about 1 mm.

All different types of elastomeric articles can be tested in accordance with the present disclosure without limitation. Such elastomeric articles include gaskets, seals, gloves, condoms, elastic bands, and the like. For example, the present disclosure is particularly well suited to testing nitrile gloves that are for use in cleanroom environments.

Nitrile rubber materials, for instance, are formed with accelerators and typically with carbamate accelerators. Carboxylated nitrile, which is a terpolymer of butadiene, acrylonitrile, and organic acid monomers, has at least two properties that make it useful for manufacturing elastomeric articles. These two features are high strength and impermeability to certain hydrocarbon solvents and oils. Compounding and curing the rubber (which is used in latex form for, e.g., dipping to provide articles of manufacture such as gloves or condoms) with other ingredients such as curing agents, accelerators, and activators is generally performed to optimize these properties. The level of each monomer in the polymer and the level of curing affect the levels of strength and the chemical resistance in the finished article. Polymers with higher levels of acrylonitrile tend to have better resistance to aliphatic oils and solvents, but are also stiffer than polymers that have lower levels of acrylonitrile. While the chemical nature of the monomers from which the polymer is made offers some degree of chemical resistance, when the polymer molecules are chemically crosslinked, resistance to chemical swelling, permeation, and dissolution greatly increase.

Crosslinking also increases the strength and elasticity of the rubber. Carboxylated nitrile latexes can be chemically crosslinked in at least two ways: the butadiene subunits can be covalently crosslinked with sulfur/accelerator systems; and the carboxylated (organic acid) sites can be ionically crosslinked with metal oxides or salts. Sulfur crosslinks often result in large improvements in oil and chemical resistance. Ionic crosslinks, resulting from, for example, the addition of zinc oxide to the latex, result in a rubber having high tensile strength, puncture resistance, and abrasion resistance, as well as high elastic modulus (a measure of the force required to stretch a film of the rubber), but poor oil and chemical resistance. Many conventional rubber formulations generally employ a combination of the two curing mechanisms.

Accelerators that can be used to produce the elastomeric articles include various carbamates. For instance, metal dialkyldithiocarbamates are commonly used as accelerators in producing nitrile elastomeric products. Such accelerators include zinc diethyldithiocarbamate, zinc dibutyldithiocarbamate, and mixtures thereof. In some embodiments, the polymer is crosslinked to a lesser degree in order to lower elastic modulus.

Although accelerators can improve the properties of the resulting elastomeric article and/or can provide process efficiencies, recent governmental regulations have required changes in formulations that have led to the presence of residual accelerators and/or carbamates present on the elastomeric articles. The present disclosure is directed to a method for detecting for the presence of residual carbamates and, in one embodiment, determining the concentration of residual carbamates on the elastomeric article.

The present disclosure is generally directed to a simple and rapid test for determining the propensity of an elastomeric article to stain or discolor. If quantification is desired, the present disclosure is also directed to an analysis that cannot only determine the propensity of an elastomeric article to discolor, but can also provide carbamate concentration on the elastomeric article.

I. Rapid Test

As described above, one aspect of the present disclosure is directed to a quick and rapid test for determining the propensity of an elastomeric article, particularly a nitrile article, to discolor. The method includes contacting the elastomeric article with a metal solution, such as a transition metal solution. The metal solution can be, for instance, a copper solution, a cobalt solution and/or a nickel solution. In one aspect, the metal solution is a metal acetate solution, such as a copper acetate solution. The elastomeric article can be contacted with the copper acetate solution using any suitable technique or method. For example, in one embodiment, the copper acetate solution can be sprayed onto the elastomeric article. Alternatively, the elastomeric article can be dipped into the copper acetate solution.

In accordance with the present disclosure, after a relatively short period of time, the elastomeric article can then be visually inspected for areas of staining and/or discoloration, especially a yellow discoloration. The amount of time needed for staining to show can be generally greater than about 5 minutes, such as greater than about 10 minutes, such as greater than about 15 minutes, and generally less than about 2 hours, such as less than about 1 hour, such as less than about 45 minutes, such as less than about 30 minutes, such as less than about 20 minutes.

In general, any suitable metal solution that reacts with residual carbamate and causes a discoloration can be used in this test. In one aspect, a copper solution is used although cobalt solutions or nickel solutions may also be used. Copper acetate has been found to be particularly effective.

In one embodiment, a saturated or substantially saturated metal solution is used to test the elastomeric articles. For example, in one embodiment, copper acetate can be combined with acetone. For instance, copper acetate can be added in an amount greater than needed to form a saturated copper acetate solution in acetone at the temperature of mixing, such as an ambient temperature. Once copper acetate has been added to acetone in the amounts described above, the resulting solution can be shaken and allowed to sit for a period of time sufficient for any undissolved copper acetone to fall to the bottom of the vessel. The resulting solution can then be filtered to remove any undissolved copper acetate and placed in an acetone resistant bottle for application to an elastomeric article.

In one particular embodiment, for instance, 500 mg of copper acetate is added to 100 mL of acetone. These ratios have been found to produce a saturated copper acetate solution in acetone at ambient temperature.

II. Quantification Test

The present disclosure is also directed to a test for determining not only the presence of residual accelerators on the elastomeric article but also for determining the concentration of the residual accelerators or carbamates. In this test, an extract is obtained from an elastomeric article and then combined with a copper solution, such as a copper acetate solution. The resulting solution is then tested for absorbance at a particular wavelength using spectrophotometry. The absorbance can then be easily compared to a standard or reference data for determining concentration.

In order to determine accelerator or carbamate concentration on an elastomeric article, the elastomeric article is first contacted with an extractant. Any suitable extractant can be used capable of removing accelerator or carbamate from the elastomeric article. The extractant, for instance, can be acetone.

In one embodiment, the elastomeric article or a portion of the elastomeric article can be submerged in the extractant and shaken. The elastomeric article can remain in contact with the extractant for a suitable period of time, such as greater than about 10 minutes, such as greater than about 15 minutes, such as greater than about 20 minutes, and generally less than about 1 hour, such as less than about 40 minutes, such as less than about 35 minutes. The amount of time the elastomeric article remains in contact with the extractant may be reduced if the elastomeric article and extractant are subject to shaking or sonication during contact.

After contact with the elastomeric article, the extractant is then combined with a controlled amount of a solution capable of reacting with the carbamate or accelerator. For example, in one embodiment, the extractant can be contacted with a copper solution, such as a copper acetate solution. For example, the extractant may be contacted with a saturated copper acetate solution. The resulting solution will discolor, such as turn yellow, if accelerator or carbamate is present.

The resulting extractant and copper acetate solution can then be tested for absorbance at a desired wavelength using a spectrophotometer. For instance, absorbance can be measured at a wavelength of generally greater than about 100 nm, such as greater than about 200 nm, such as greater than about 300 nm, and generally less than about 700 nm, such as less than about 600 nm, such as less than about 500 nm, such as less than about 400 nm. In one particular embodiment, absorbance is measured at a wavelength of 433 nm. Any suitable spectrophotometer can be used to measure absorbance. Spectrophotometers that can be used include, for instance, the HACH 3900 spectrophotometer. In addition, various other spectrophotometers can be used.

The measure at absorbance of the extract and copper acetate solution can then be compared to a known standard for determining the concentration of carbamate on the elastomeric article. For example, stock solutions can be prepared of known concentration of carbamate in copper acetate. The absorbance of the stock solutions can be measured and used to form a graph of absorbance versus concentration. The absorbance of the extract and copper acetate solution can then be compared to the graph for determining carbamate concentration on the elastomeric article. In one aspect, the elastomeric article may have a propensity for staining when the measured carbamate concentration is greater than about 0.5 ppm, such as greater than about 1 ppm.

The method and process of the present disclosure can be tailored to a particular carbamate or to a mixture of carbamates that are used to produce the elastomeric article. For example, known accelerators include zinc diethyldithiocarbamate, zinc dibutyldithiocarbamate, and mixtures thereof. The stock solutions can be formed from the particular carbamate or mixture of carbamates that are used in the process of producing the elastomeric article for comparison to the absorbance measurement of the extractant and copper acetate solution.

III. Remedial Actions

If either of the above tests (or both of the above tests together) indicate that the elastomeric articles being tested have a propensity to discolor or stain, various remedial actions can be taken at the manufacturing facility in order to remediate the problem and prevent future staining issues. For example, in one aspect, the elastomeric articles can be washed. Any suitable washing fluid can be used including water. For example, in one aspect, the elastomeric articles can be washed in distilled water.

In addition to washing the elastomeric articles after the articles are formed, various other steps can be taken during the process of making the articles to reduce the propensity of the articles to stain. For example, the formulation for producing the elastomeric article can be modified. In one aspect, for example, a greater amount of crosslinking agent may be added to the formulation for reacting with the accelerator. In this manner, the amount of residual accelerator left in the article is reduced. Alternatively, less accelerator can be added to the formulation.

In still another embodiment, temperature or pH changes can occur within the process that promotes more robust reaction between the accelerator and the other components used to produce the elastomeric article.

In one embodiment, more than one of the above remediation steps may be taken in order to prevent staining.

The present disclosure may be better understood with reference to the following example.

Example

When determining the concentration of accelerator contained in an elastomeric article, particularly a nitrile glove, as would be understood by one skilled in the art, the stock solutions and relative amounts of components can be varied depending upon the type of spectrophotometer used. The following are two different procedures for using two different spectrophotometers in accordance with the present disclosure.

Preparation of Reagents

Cu Acetate: Dissolve 500 mg of Cu acetate in 100 mL of $H_2O$

Zinc diethyldithiocarbamate (ZDEC) and Zinc dibutyldithiocarbamate (ZDBC) standards—Weight 50 mg and dissolve in 100 mL acetone=500 ppm

*ppm-µg/mL.* e.g. 1 ppm means 1 µg of compound is present 1 mL of solvent, 100 ppm-100 µg/mL and 500 ppm=500 µg/mL.

Procedure—To be used with HACH 3900 Spectrophotometry

Weigh Glove and place in Jar

Add 100 mL of Acetone, shake gently. Leave for 30 min.

After 30 min take 0.25 mL of extract, add 9.75 mL of acetone, then add 50 µL of the prepared Cu acetate solution. The solution will turn yellow.

Wait 5 min and read absorbance at 433 nm.

If precipitate is formed wait for it to settle and decant gently into a cuvette.

Make mixed standard dilutions form the 500 pm stock solution. 100, 75, 50, 25, 12.5 ppm (exact range will depend on spectrophotometer and the amount of accelerator in glove).

100 ppm—Take 20 mL of ZDEC and 20 mL of ZDBC stock solution in 100 ml vol flask. Bring to volume with acetone.

The rest of the dilutions will be made from this 100 ppm solution. Refer to table 1

E.g. 50 ppm—take 5 mL of 100 ppm standard+5 mL acetone. Add 50 µL of the prepared Cu acetate solution. Mix gently and then read absorbance Take 10 mL of prepared standard, add 50 µL of Cu acetate solution and read absorbance.

If measuring only ZDEC or ZDBC make a separate standard curve using only the accelerator that is being measured.

TABLE 1

| Dilutions from 100 ppm standard | | |
| --- | --- | --- |
| Concentration | Vol of 100 ppm standard | Vol of acetone |
| 75 | 7.5 | 2.5 |
| 50 | 5 | 5 |
| 25 | 2.5 | 7.5 |
| 12.5 | 1.25 | 8.75 |

Plot a standard curve with concentration on the x axis and absorbance on the y axis. Use the linear curve equation to calculate the concentration of the samples.

For samples—try an initial dilution for reading (0.25 mL sample+9.75 mL acetone). Read the absorbance. Read 2-3 times to make sure that the reading is stable. If it does not stabilize after 3 readings, dilute further.

If this initial concentration is too dilute, try and run either a ½ dilution or an undiluted sample.

The absorbance of the sample should be between the lowest and the highest standard. If it is out of this range adjust the dilution of the sample extract and read again.

Calculation

Concentration of sample extract in ppm. Y intercept and slope is obtained from the standard curve.

$$\frac{Abs - y\ intercept}{Slope} \times Dli\ Factor$$

$$\text{Concentration in glove}\ \mu g/g = \frac{ppm\ \text{from above} \times 10\ mL}{wt\ of\ glove}$$

10 mL is the total volume of the extract, so this gives us the total amount that was present in the glove.

Referring to FIG. 1, absorbance versus a concentration of a mixture of ZDEC and ZDBC is shown.

Procedure 2: To be used with other spectrophotometer with 1.5 mL cuvettes

When using other spectrophotometers, the following procedure may be used.

Weigh Glove and place in Jar

Add 100 mL of Acetone, shake gently. Leave for 30 min.

After 30 min take 2 mL of extract, add 10 µL of Cu acetate solution. The solution will turn yellow. If the extract is too concentrated make appropriate dilutions.

Transfer to cuvette and read absorbance at 433 nm.

If ppt is formed wait for it to settle and decant gently into the cuvette.

Make mixed standard dilutions—Range from 100-2 ppm (exact range will depend on spectrophotometer and the amount of accelerator in glove)

Take 2 mL of standard, add 10 µL of Cu acetate solution and read absorbance.

Figure 2:
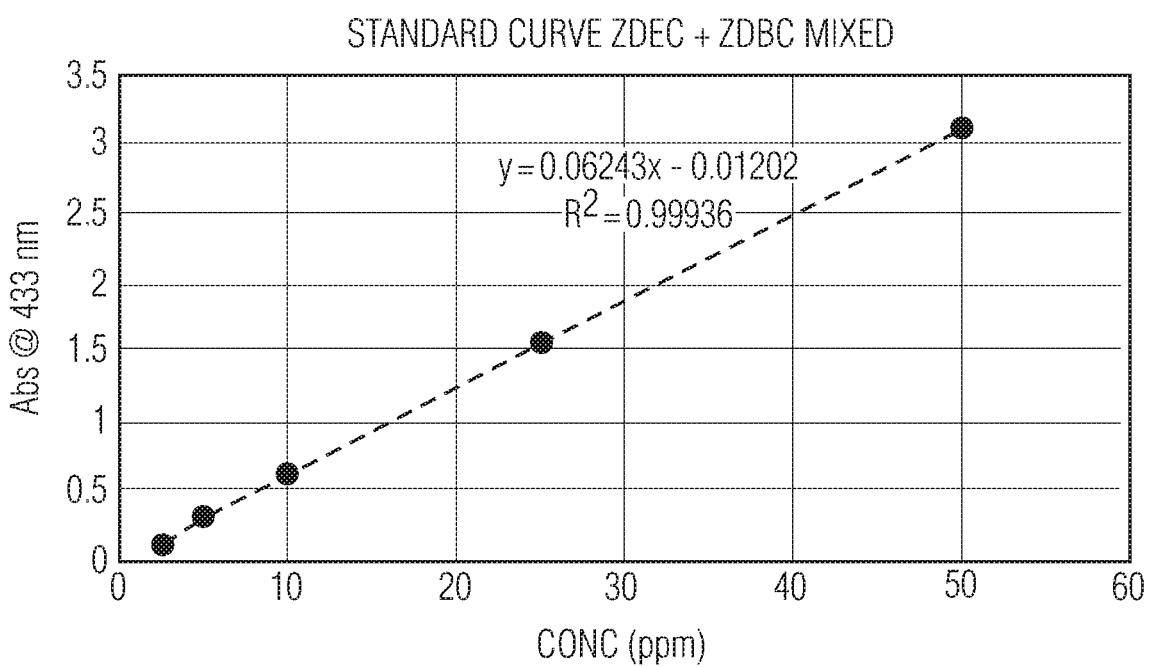
FIG. 2 is a graph illustrating another embodiment of absorbance versus concentration relationship for a mixture of zinc diethyldithiocarbamate and for zinc dibutyldithiocarbamate.
Figure 3:
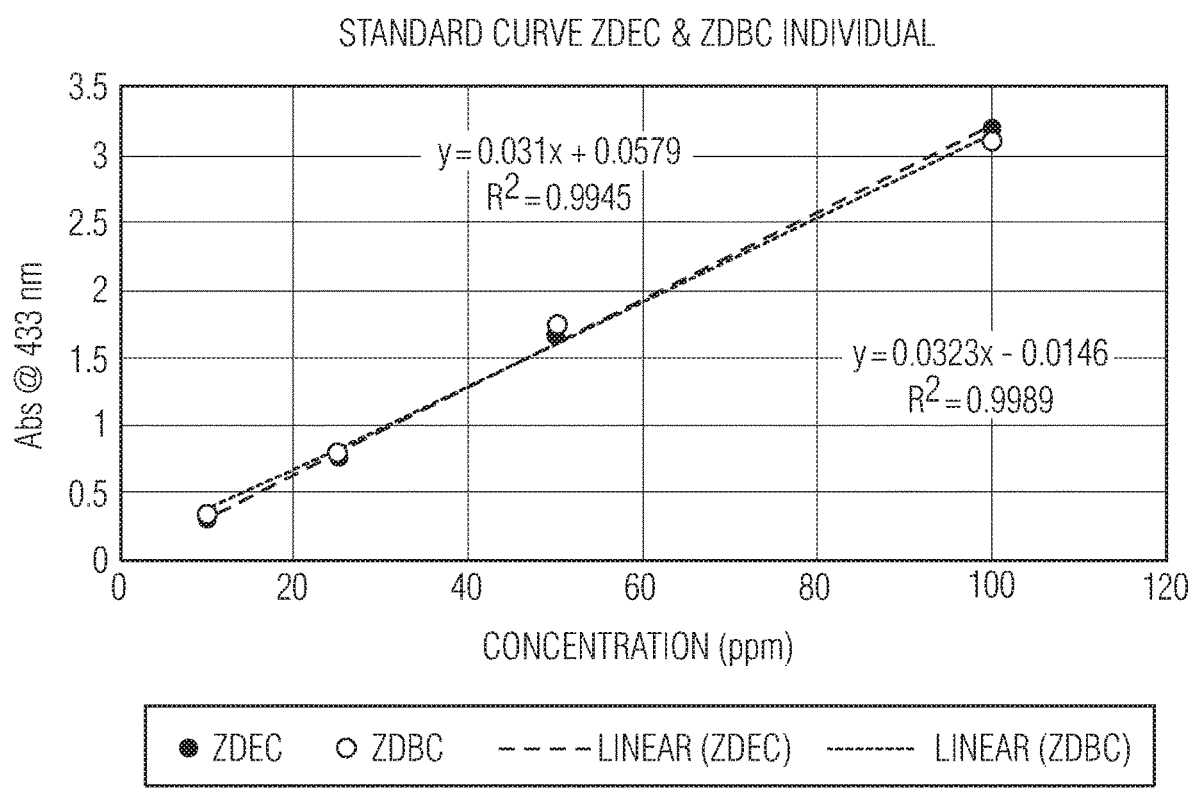
FIG. 3 is a graph illustrating absorbance versus concentration relationship for zinc diethyldithiocarbamate and for zinc dibutyldithiocarbamate individually.

Referring to FIGS. 2 and 3, absorbance versus concentration standardized curves are illustrated. In FIG. 2, the graph was produced using a mixture of ZDEC and ZDBC. In FIG. 3, on the other hand, standard curves are shown for each carbamate individually.

Both, the mixed standard solutions and the individual standard individual produced acceptable standard curves across a wide range of concentrations.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A method for determining an elastomeric articles propensity for staining comprising:
    contacting an elastomeric article with a transition metal solution, wherein the elastomeric article is made from a nitrile polymer, wherein the transition metal solution is a saturated copper acetate solution, wherein the saturated transition metal solution comprises a ratio of 5 mg copper acetate per 1 mL of acetone; and
    testing the elastomeric article for the propensity of the elastomeric article to stain, wherein the elastomeric article is tested for staining by allowing the contacted elastomeric article and transition metal solution to dwell for a period of time and visually observing the elastomeric article for discoloration, wherein the period of time ranges from 5 minutes to 2 hours.

2. The method as defined in claim 1, wherein the discoloration is a yellow discoloration.

3. The method as defined in claim 1, wherein the copper acetate solution is sprayed onto a surface of the elastomeric article.

4. The method as defined in claim 1, wherein the elastomeric article is dipped into the transition metal solution.

5. The method as defined in claim 1, wherein the elastomeric article is a glove.

6. A method for determining residual carbamate compounds on elastomeric articles comprising:
    submerging an elastomeric article in an extractant for a period of time such that an extract is obtained, wherein the elastomeric article is shaken in the extractant, wherein the period of time ranges from 10 minutes to 1 hour, wherein the extractant is an acetone solution, wherein the elastomeric article is made from a nitrile polymer;
    contacting the extract obtained from the elastomeric article with a transition metal solution wherein the transition metal solution is a saturated or a nearly saturated copper acetate solution, wherein the saturated transition metal solution comprises a ratio of 5 mg copper acetate per 1 mL of acetone;
    visually observing the coloration of the transition metal solution contacted with the extract, wherein the color yellow indicates a presence of carbamate;
    measuring an absorbance of the extract and transition metal solution at a wavelength using spectrophotometry; and
    comparing the measured absorbance with reference data in order to determine a concentration of carbamate on the elastomeric article.

\* \* \* \* \*